United States Patent [19]
Fill et al.

[11] Patent Number: 5,908,297
[45] Date of Patent: Jun. 1, 1999

[54] DENTAL VACUUM SYSTEM WITH FOOT-ACTUATED VALVE

[75] Inventors: David Fill, Hermitage; Robert J. Krupinski, Coraopolis, both of Pa.

[73] Assignee: David Fill, D.D.S., Hermitage, Pa.

[21] Appl. No.: 08/831,061

[22] Filed: Apr. 1, 1997

[51] Int. Cl.⁶ .................................................. A61C 17/06
[52] U.S. Cl. ............................. 433/95; 433/91; 433/101; 433/116
[58] Field of Search .................................. 433/91, 92, 95, 433/101, 116; 251/230, 295

[56] References Cited

U.S. PATENT DOCUMENTS

| | | |
|---|---|---|
| 802,954 | 10/1905 | Waterman . |
| 3,138,873 | 6/1964 | Bishop ...................................... 433/92 |
| 3,489,390 | 1/1970 | Cadogan . |
| 4,158,916 | 6/1979 | Adler . |
| 4,242,088 | 12/1980 | Ekman ..................................... 433/101 |
| 4,723,912 | 2/1988 | Nieusma ................................. 433/116 |
| 4,810,194 | 3/1989 | Snedden ..................................... 433/91 |
| 5,226,629 | 7/1993 | Millman et al. ......................... 251/295 |
| 5,228,851 | 7/1993 | Burton ..................................... 433/116 |
| 5,267,860 | 12/1993 | Ingram, Jr. et al. .................... 433/116 |
| 5,531,722 | 7/1996 | Van Hale ................................. 604/280 |

FOREIGN PATENT DOCUMENTS

| | | |
|---|---|---|
| 3627144A1 | 5/1987 | Germany . |
| WO 95/01759 | 1/1995 | WIPO . |

OTHER PUBLICATIONS

American Dental Accessories Catalog, pp. 41, 53; Fall 1995.

*Primary Examiner*—John J. Wilson
*Attorney, Agent, or Firm*—Kirkpatrick & Lockhart LLP

[57] ABSTRACT

A dental vacuum system having a foot-actuated valve for controlling the flow of vacuum through the system. The foot-actuated valve is located away from the field of operation such that the valve is not exposed to the typical sources of pathogenic contaminants in a dental office.

9 Claims, 4 Drawing Sheets

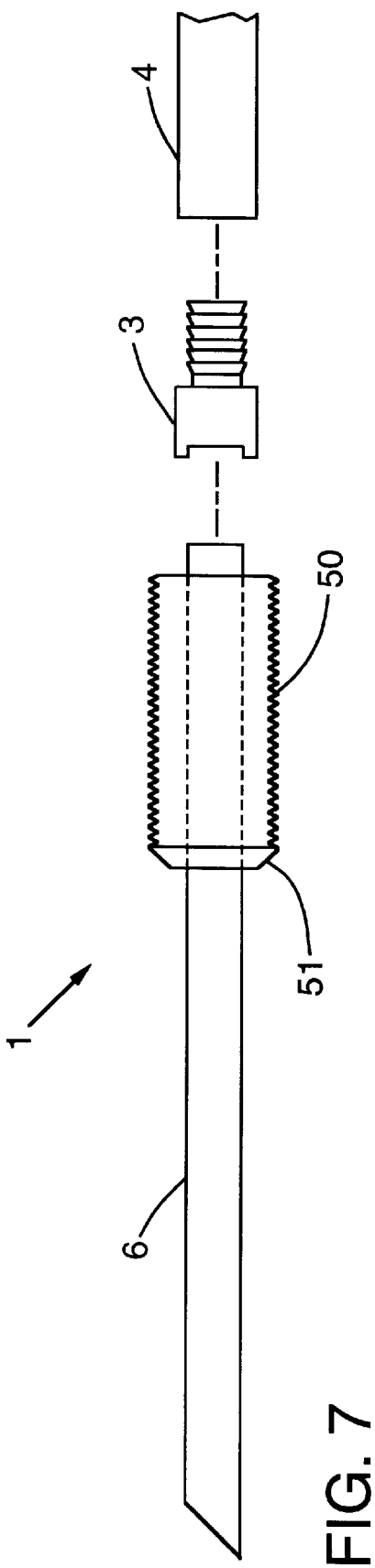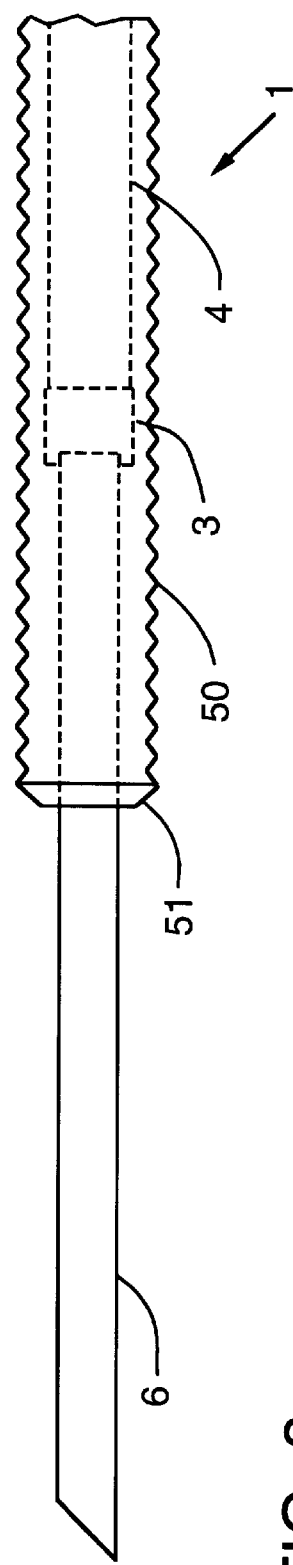

DENTAL VACUUM SYSTEM WITH FOOT-ACTUATED VALVE

CROSS REFERENCE TO RELATED APPLICATIONS (Not Applicable)

FEDERALLY SPONSORED RESEARCH OR DEVELOPMENT (Not Applicable)

BACKGROUND OF THE INVENTION

1. Field of the Invention

The present invention relates to dental vacuum systems and, more particularly, is directed to a dental vacuum system with a foot-actuated pedal vacuum valve that is used to control the vacuum flow to various handheld dental instruments such that the valve is located away from the patient's proximity to decrease the risk of the transmission of pathogenic contaminants between patients and between patients and the dental office staff.

2. Description of the Background of the Invention

In the typical dental office, blood, saliva and particulates are not confined to the area inside the patient's mouth during dental procedures and operations. Blood and saliva have a tendency to spray and splatter during certain dental procedures. Blood, saliva and particulates often collect on dental instruments and surfaces in proximity to the patient's mouth, including the handheld instruments that are used during the dental procedure. The blood and saliva of patients can carry pathogenic contaminants which may cause infectious diseases such as the common cold, pneumonia, tuberculosis, herpes, hepatitis B, and acquired immune deficiency syndrome (AIDS). Such contaminants place other patients and dental workers at risk of contracting infectious diseases. The United States Centers for Disease Control has issued universal precautions that should be followed by all health care professionals while performing dental procedures and operations. According to the precautions, all human blood and saliva should be treated as if they are known to be infected with the HIV virus, hepatitis B, or some other bloodborne pathogen.

FIG. 1 shows a typical HVE device (1). HVE valve body (2) is connected by means of tubing connector base (3) to HVE tubing (4). The vacuum flow through the HVE device is controlled by means of HVE valve control (5). The HVE valve control (5) is typically a rotary or lever type control mechanism. HVE tip (6), which can either be a metal aspirator tip or a flexible plastic evacuator tip, is attached to the HVE valve body (2) and is typically placed in the patient's mouth to evacuate saliva, blood, and other particulates, such as tooth fragments, that are present during a dental procedure.

In the typical dental office, a dental vacuum system, as depicted in FIG. 2 as (7), which includes a high volume evacuator (HVE), a saliva ejector (SE), or both, is used to evacuate blood, saliva and particulates from the patient's mouth during a dental procedure. As shown in FIG. 2, the HVE device (1) of FIG. 1 is part of the dental vacuum system (7). Central vacuum unit (8) provides the vacuum required for evacuation of the system. Hose (9) is connected between the central vacuum unit (8) and vacuum collection canister (10). The vacuum collection canister (10) is used as a junction for the vacuum system and also typically contains a filter for filtering particulates from the vacuum system. The HVE tubing (4), which has the HVE device (1) connected to it, is in turn connected to the vacuum collection canister (10). It is understood by those skilled in the art that the dental vacuum system (7) of FIG. 2 could also contain a saliva ejector device in addition to or in place of the HVE device as shown.

During dental procedures, the outside surfaces of all dental handpieces that are used during the procedure become contaminated. This includes handpieces, such as the HVE device (1), because the device is used in close proximity to the patient's mouth. As can be seen from FIG. 1, the HVE valve control (5) is used in close proximity to the patient's mouth, and as such has a tendency to become contaminated with fluids that are expelled from the patient's mouth. The HVE valve control (5) has moving parts that are particularly susceptible to the collection of contaminants, especially contaminants that are evacuated through the HVE valve inside the HVE valve body (2). The accumulation of such contaminants poses a risk of exposing patients and dental workers to pathogenic contaminants. Also, the HVE valve control (5) is operated manually by health care workers during the dental procedure and thus the outside of the HVE device (1) is susceptible to the accumulation of any possible contaminants that are on the valve operator's hands.

Because the HVE device (1) comes into contact with the patient's tissue and is in close proximity to the performance of the dental procedure, the HVE device (1) must undergo sterilization and disinfection, or asepsis. In particular, the HVE device (1) must be sterilized after each use. Sterilization methods include steam sterilization using an autoclave, dry heat sterilization, and chemical vapor sterilization. The HVE valve body (2) must be disassembled for proper cleaning and sterilization.

Thus, there is a need for a dental vacuum system that provides protection against pathogenic contaminants while isolating moving parts from infectious debris and contaminants.

SUMMARY OF THE INVENTION

In accordance with the present invention, there is provided a dental vacuum system which has a foot-actuated valve that is located away from the proximity of the dental procedure. The vacuum system comprises a vacuum collection canister and a hose. Interposed between the hose and the vacuum collection canister is a foot-actuated valve which is used to control the flow of vacuum to the device. The vacuum system may include a foot-actuated valve that controls just an HVE device, just an SE device, or both an SE and an HVE device. The HVE or SE devices may have disposable covers which cover the tubing connector bases. There is also provided a method for locating the foot-actuated valve in which the valve is connected to at least two sections of hose such that the valve is located away from the field of operation.

It is an object of the present invention to provide a dental vacuum system with a foot-actuated valve that is located away from the field of operation such that operation of the valve does not promote the transmission of pathogenic contaminants. It is another object of the present invention to provide a dental vacuum system with a foot-actuated valve that is located away from the field of operation to prevent the accumulation of particulates in and on the valve assembly. It is also an object of the present invention to provide a dental vacuum system with a foot actuated valve that has a one piece disposable HVE or SE and barrier device which covers in an extended position, a portion of the tubing connector bases of the HVE and SE barrier devices. It is yet another object of the present invention to provide a method of locating a foot-actuated valve in such a position as to be located away from the field of operation.

BRIEF DESCRIPTION OF THE DRAWINGS

In the accompanying drawings, there is shown preferred embodiments of the invention wherein like reference numerals are employed to designate like parts and wherein:

FIG. 7 is a view of a disposable one piece HVE and barrier device in the unextended position; and FIG. 8 is a view of a disposable one piece HVE and barrier device in the extended position.

DETAILED DESCRIPTION OF THE INVENTION

Referring now to the figures for the purposes of illustrating a present preferred embodiment of the invention only and not for purposes of limiting the same, the figures show a dental vacuum system with a foot-actuated valve which is located outside the proximity of the field of operation. The skilled artisan will readily appreciate, however, that the subject invention can be constructed with the foot-actuated valve located in various positions in order to achieve the same result.

Figure 1:
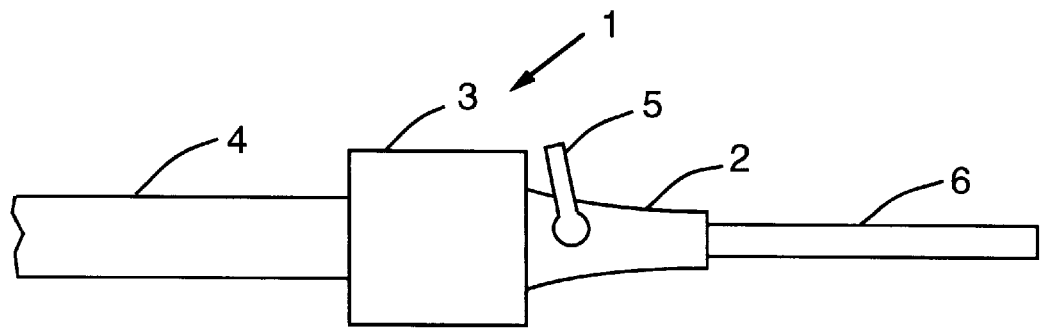
FIG. 1 is a view of a typical HVE device.
Figure 2:
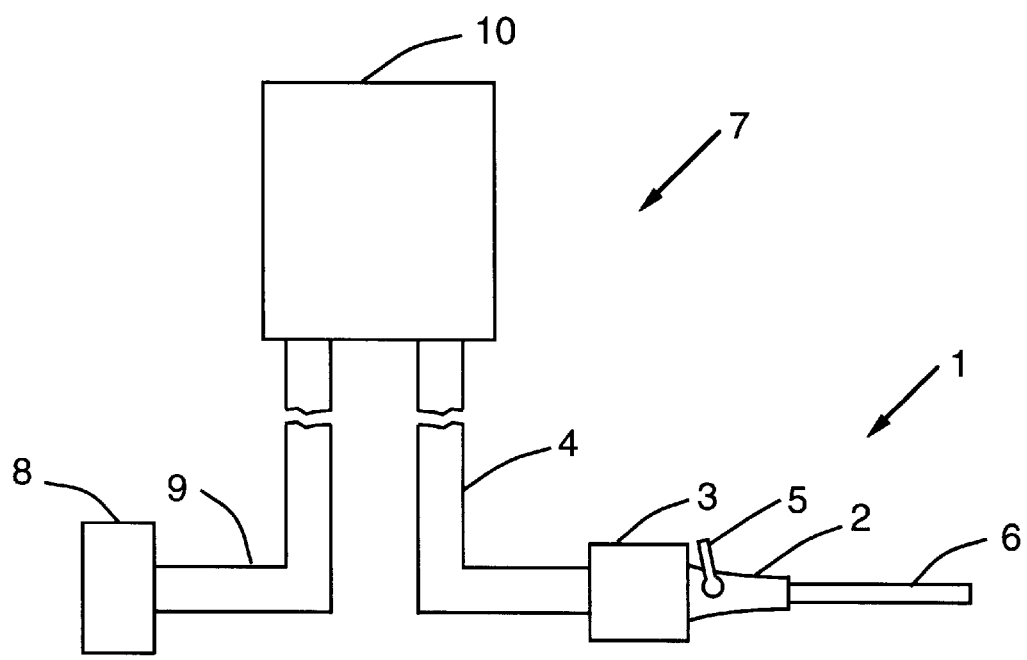
FIG. 2 is a view of a typical dental vacuum system.
Figure 3:
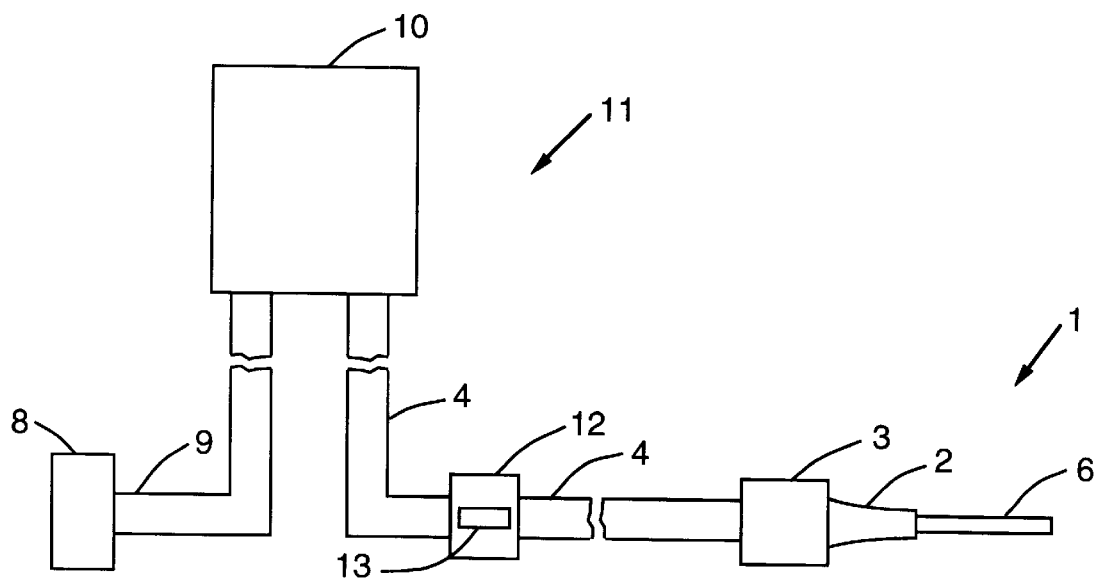
FIG. 3 is a view of a preferred embodiment of the present invention with a foot-actuated valve.

More particularly and with reference to FIG. 3, there is shown a preferred dental vacuum system, generally designated as (11), that preferably comprises a foot-actuated valve (12) located between the HVE device (1) and the vacuum collection canister (10). The foot-actuated valve (12) is attached to the HVE tubing (4) and may be positioned anywhere on the HVE tubing (4) as is practical. The foot-actuated valve (12) includes foot-actuated valve control (13) which allows for the adjustment of vacuum flow to the HVE device (1). Thus, the HVE device (1) may include a valve and valve control, but they are not necessary and would be redundant if present.

Figure 4:
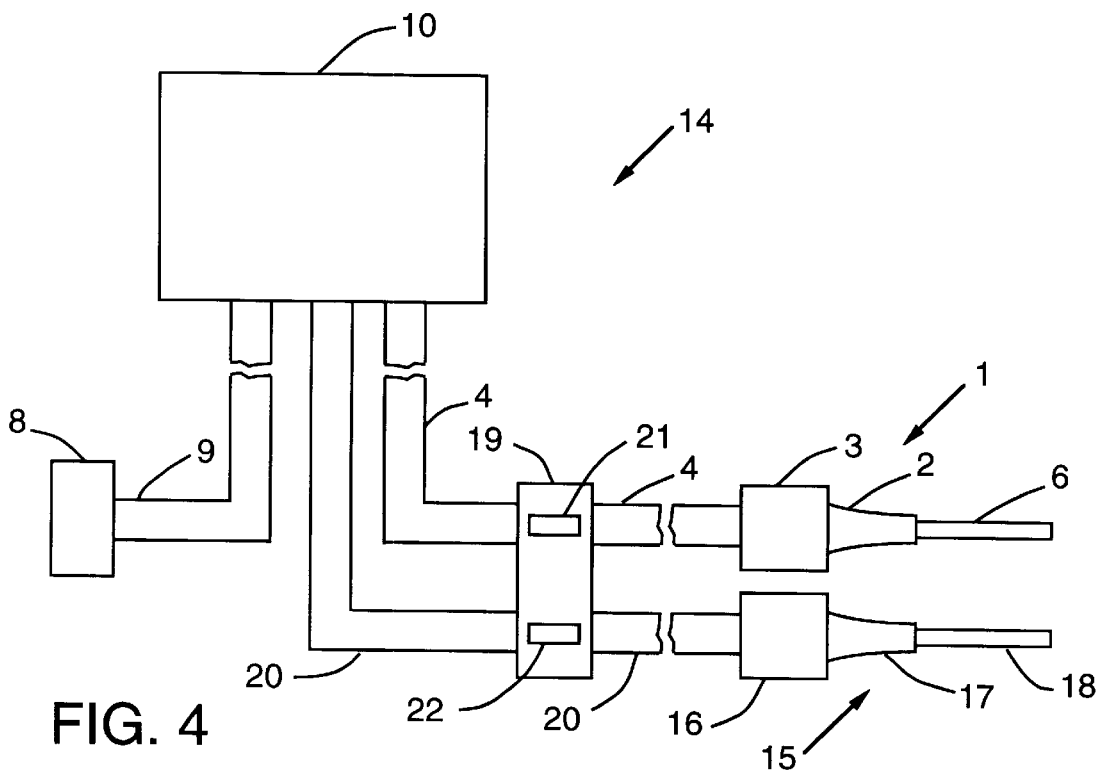
FIG. 4 is a view of a preferred embodiment of the present invention incorporating a dual foot-actuated valve.

Turning to FIG. 4, a preferred embodiment of the present invention as designated generally as (14) is shown which incorporates SE device (15). The SE device (15) comprises SE tubing connector base (16), SE valve body (17), and SE tip (18). Dual foot-actuated valve (19) is connected to SE tubing (20) and to the HVE tubing (4) between the HVE device (1) and the SE device (15) and the vacuum collection canister (10). In a preferred embodiment, the dual foot-actuated valve (19) comprises separate control mechanisms (21, 22) to independently control the vacuum flow to the SE device (15) and the HVE device (1).

Figure 5:
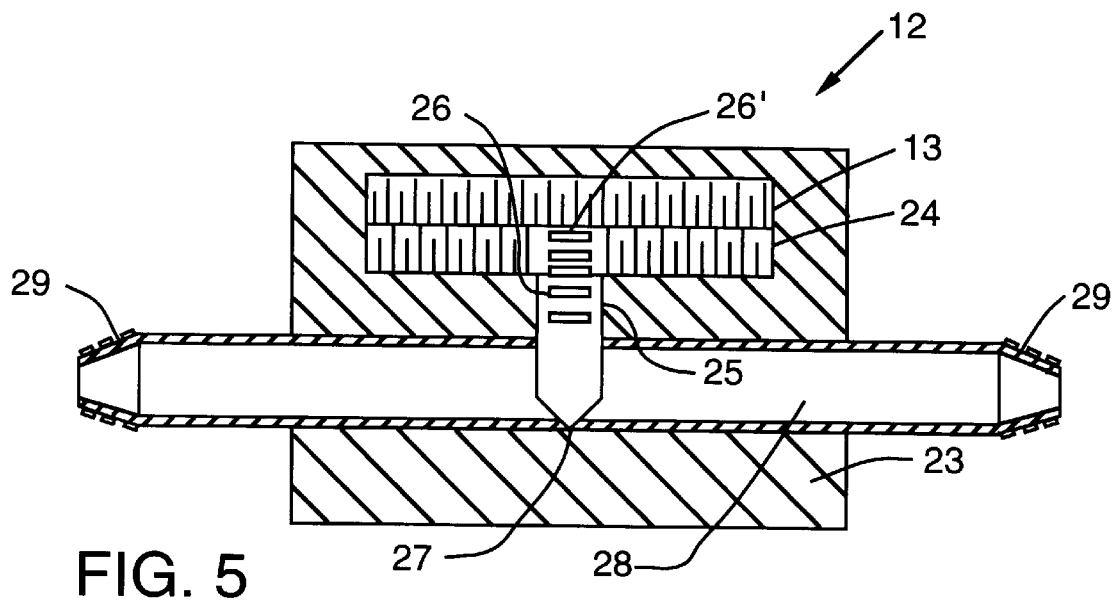
FIG. 5 is a view of a preferred embodiment of the foot-actuated valve of FIG. 3.

FIG. 5 shows a preferred embodiment of the foot-actuated valve (12) of FIG. 3. The foot-actuated valve (12) is constructed as a rotary slide valve in a preferred embodiment. The foot-actuated valve control (13) is a rotating threaded cylinder located in housing (23) and engages internal threaded cylinder (24). Rotation of the foot-actuated valve control (13) causes rotation of the internal threaded cylinder (24). Internal threaded cylinder (24) has a toothed portion (26'). Rack (25) has a plurality of teeth (26) which engage the teeth (26') of threaded cylinder (24). Valve plug (27) is attached to one end of the rack (25). Rotation of the internal threaded cylinder (24) causes the rack (25) to move perpendicularly to the internal threaded cylinder (24) and thus causes the valve plug (27) to move in or out of air flow channel (28) to restrict or permit vacuum flow to the HVE device (1), which is connected to one of a plurality of tubing connectors (29). It can be understood by those skilled in the art that the foot-actuated valve (12) may be constructed such that the valve provides variable vacuum operation or may be constructed as an on/off switch. The foot-actuated valve (12) may be of any type suitable, one such type being a pedal vacuum valve. Also, the foot-actuated valve (12) may be constructed using any valve arrangement that is commonly accepted in the art, such as a rotary stem valve or other combinations of levers involving gear movements to control stem valves.

Figure 6:
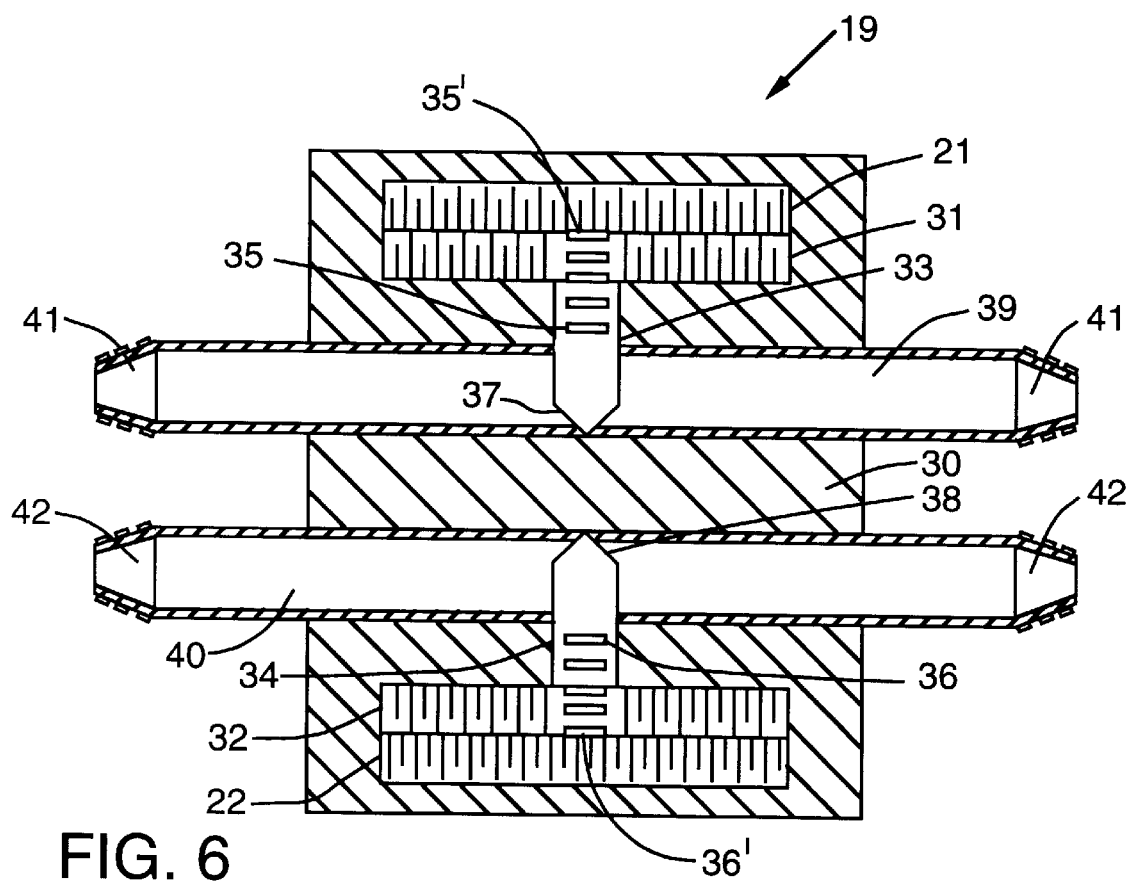
FIG. 6 is a view of a preferred embodiment of the dual foot-actuated valve of FIG. 4.

FIG. 6 shows a preferred embodiment of the dual foot-actuated valve (19). The dual foot-actuated valve (19) is constructed as a dual rotary slide valve in a preferred embodiment. Foot-actuated control mechanisms (21, 22) are rotating threaded cylinders located in housing (30) and the control mechanisms (21, 22) are operated independently to engage internal threaded cylinders (31, 32). Rotation of the control mechanisms (21, 22) causes rotation of the internal threaded cylinders (31, 32). Racks (33, 34) each have a plurality of teeth (35, 36) which engage teeth (35', 36') carried by threaded cylinders (31, 32), respectively. Valve plugs (37, 38) are attached to one end of each of the racks (33, 34). Rotation of the internal threaded cylinders (31, 32) causes the racks (33, 34) to move perpendicularly to the internal threaded cylinders (31, 32) and thus causes the valve plugs (37, 38) to move in or out of air flow channels (39, 40) to restrict or permit vacuum flow to the HVE device (1), which is connected to one of a plurality of tubing connectors (41), and to restrict or permit vacuum flow to the SE device (15), which is connected to one of a plurality of tubing connectors (42). It can be understood by those skilled in the art that the dual foot-actuated valve (19) may provide variable vacuum operation using the control mechanisms (21, 22) or may be constructed as an on/off switch. The dual foot-actuated valve (19) may be of any type suitable, one such type being a dual pedal vacuum valve. The dual foot-actuated valve (19) may be constructed using any valve arrangement that is commonly accepted in the art, such as a rotary stem valve or other combinations of levers involving gear movements to control stem valves.

FIG. 7 shows the HVE device (1), the tubing connector base (3), and the HVE tubing (4). An accordian-like barrier sleeve (50) is shown attached to the HVE tip (6) by connector ring (51) in an unextended position. The connector ring (51) may be rigidly attached to the HVE tip (6) to form a unitary disposable device or may be slidably attached to a reusable or disposable HVE tip (6). The barrier sleeve (50) may be constructed of any type of flexible material, such as plastic, that is impenetrable to fluids and liquids. The sleeve (50) is shown in an extended position in FIG. 8. The sleeve (50) covers the tubing connector base (3) and a portion of the HVE tubing (4) to prevent the transmission of pathogenic contaminants.

The sleeve (50) can be used with conventional HVE or SE devices that have conventional valves and valve bodies. The sleeve (50) may also be used with HVE or SE devices that do not have conventional valves and valve bodies but are instead controlled by a pedal vacuum valve. The sleeve (50) may be provided with a ring, tab, or other device at one end to facilitate movement from the unextended position of FIG. 7 to the extended position of FIG. 8.

The present invention provides solutions to the problem of pathogenic contaminants collecting on dental handpieces that are present with such devices that are in use today. It will be understood, however, that various changes in the details, materials, and arrangements of parts which have been herein described and illustrated to explain the nature of the invention may be made by those skilled in the art within the principle and scope of the invention as expressed in the appended claims.

What is claimed is:

1. A dental vacuum system comprising:
   a vacuum collection canister;
   at least one foot-actuated valve comprising:
   a housing having at least one air flow channel;
   at least one valve control mechanism located in said housing;
   at least one internal threaded cylinder, said internal threaded cylinder oriented in parallel to said air flow channel and threadably engaged to said valve control mechanism;
   at least one rack having a plurality of teeth engaged with said internal threaded cylinder; and
   at least one valve plug located in said air flow channel and attached to an end of said rack such that rotation of said internal threaded cylinder causes said valve plug to move in or out of said air flow channel to block or unblock portions of said air flow channel;
   a first section of hose having a first end and a second end, said first end connected to said vacuum collection canister and said second end connected to said foot-actuated valve; and
   a second section of hose having a first end and a second end, said first end connected to said foot-actuated valve and said second end adapted for connection to a handheld dental device.

2. The dental vacuum system of claim 1 further comprising at lease one handheld dental device connected to said second end of said second section of hose.

3. The dental vacuum system of claim 1 further comprising:
   a central vacuum unit; and
   a third section of hose having a first end and a second end, said first end connected to said central vacuum unit and said second end connected to said vacuum collection canister.

4. A dental vacuum system comprising;
   at least one handheld dental device;
   a vacuum collection and filtration canister;
   at least one foot-actuated pedal vacuum valve comprising:
   a housing having at least one air flow channel;
   at least one valve control mechanism located in said housing;
   at least one internal threaded cylinder, said internal threaded cylinder oriented in parallel to said air flow channel and threadably engaged to said valve control mechanism;
   at least one rack having a plurality of teeth engaged with said internal threaded cylinder; and
   at least one valve plug located in said air flow channel and attached to an end of said rack such that rotation of said internal threaded cylinder causes said valve plug to move in or out of said air flow channel to block or unblock portions of said air flow channel;
   a first section of vacuum hose having a first end and a second end, said first end connected to said foot-actuated pedal vacuum valve and said second end connected to said vacuum collection and filtration canister; and
   a second section of vacuum hose having a first end and a second end, said first end connected to said foot-actuated pedal valve and said second end connected to said handheld dental device.

5. The dental vacuum system of claim 4 further comprising:
   a central vacuum source; and
   a third section of vacuum hose having a first end and a second end, said first end connected to said central vacuum source and said second end connected to said vacuum collection and filtration canister.

6. A foot-actuated valve adapted for use in a dental vacuum system comprising:
   a housing having at least one air flow channel;
   at least one valve control mechanism located in said housing;
   at least one internal threaded cylinder, said internal threaded cylinder oriented in parallel to said air flow channel and threadably engaged to said valve control mechanism;
   at least one rack having a plurality of teeth engaged with said internal threaded cylinder; and
   at least one valve plug located in said air flow channel and attached to an end of said rack such that rotation of said internal threaded cylinder causes said valve plug to move in or out of said air flow channel to block or unblock portions of said air flow channel.

7. A dental vacuum system comprising;
   at least one handheld dental device;
   a vacuum collection and filtration canister;
   at least one foot-actuated pedal vacuum valve comprising:
   a housing having at least one air flow channel;
   at least one valve control mechanism located in said housing;
   at least one internal threaded cylinder, said internal threaded cylinder oriented in parallel to said air flow channel and threadably engaged to said valve control mechanism;
   at least one rack having a plurality of teeth engaged with said internal threaded cylinder; and
   at least one valve plug located in said air flow channel and attached to an end of said rack such that rotation of said internal threaded cylinder causes said valve plug to move in or out of said air flow channel to block or unblock portions of said air flow channel;
   a first section of vacuum hose having a first end and a second end, said first end connected to said foot-actuated pedal vacuum valve and said second end connected to said vacuum collection and filtration canister;
   a second section of vacuum hose having a first end and a second end, said first end connected to said foot-actuated pedal valve and said second end connected to said handheld dental device; and
   a nonpermeable sleeve attached to said handheld dental device and covering a portion of said handheld dental device and a portion of said second end of said second section of vacuum hose.

8. The dental vacuum system of claim 7 wherein said nonpermeable sleeve has a connector ring, said connector ring attached to said handheld dental device.

9. A dental vacuum system, comprising:
   at least one handheld dental device having a unitary disposable portion, said unitary disposable portion including a vacuum tip and an accordian-like barrier sleeve connected to said vacuum tip;
   a vacuum collection and filtration canister;
   at least one foot-actuated pedal vacuum valve comprising:
      a housing having at least one air flow channel;
      at least one valve control mechanism located in said housing;
      at least one internal threaded cylinder, said internal threaded cylinder oriented in parallel to said air flow channel and threadably engaged to said valve control mechanism;
      at least one rack having a plurality of teeth engaged with said internal threaded cylinder; and
      at least one valve plug located in said air flow channel and attached to an end of said rack such that rotation of said internal threaded cylinder causes said valve plug to move in or out of said air flow channel to block or unblock portions of said air flow channel;
   a first section of vacuum hose having a first end and a second end, said first end connected to said foot-actuated pedal vacuum valve and said second end connected to said vacuum collection and filtration canister; and
   a second section of vacuum hose having a first end and a second end, said first end connected to said foot-actuated pedal vacuum valve and said second end connected to said handheld dental device.

* * * * *